United States Patent
Alston, Jr. et al.

(10) Patent No.: US 9,320,566 B1
(45) Date of Patent: Apr. 26, 2016

(54) APPLICATOR FOR INSERTING AN ENLARGED LENS ONTO AN EYE OF A USER

(71) Applicants: Timothy Edgar Alston, Jr., Sanford, NC (US); Eric Emmanual Alston, Fuquay-Varina, NC (US)

(72) Inventors: Timothy Edgar Alston, Jr., Sanford, NC (US); Eric Emmanual Alston, Fuquay-Varina, NC (US)

( * ) Notice: Subject to any disclaimer, the term of this patent is extended or adjusted under 35 U.S.C. 154(b) by 538 days.

(21) Appl. No.: 13/689,557

(22) Filed: Nov. 29, 2012

Related U.S. Application Data

(60) Provisional application No. 61/630,281, filed on Dec. 8, 2011.

(51) Int. Cl.
  *A61F 9/00* (2006.01)
  *A61B 19/00* (2006.01)

(52) U.S. Cl.
  CPC ............. *A61B 19/00* (2013.01); *A61F 9/0061* (2013.01)

(58) Field of Classification Search
  CPC ....... A61F 9/0061; A61F 2/1662; A61F 9/00; A44C 9/0061; A44C 9/0069; A44C 9/0053; A44C 9/00
  USPC .......... 623/6.12; 606/107; 294/1.2; 224/217, 224/218, 148.1; 433/163; 206/37, 5.1; 401/8; 2/160; 63/1.11, 1.12, 1.14, 15; D14/427
  See application file for complete search history.

(56) References Cited

U.S. PATENT DOCUMENTS

| | | | | |
|---|---|---|---|---|
| 1,319,251 A | * | 10/1919 | Schless | A44C 17/02 63/26 |
| D159,495 S | * | 8/1950 | Linden | A44C 17/02 206/37 |
| 3,132,887 A | * | 5/1964 | Martinez | A61F 9/0061 294/1.2 |
| 3,327,391 A | * | 6/1967 | Malm | 433/163 |
| 3,490,806 A | * | 1/1970 | Lopez-Calleja et al. | 294/1.2 |
| 3,897,968 A | | 8/1975 | Allen, Jr. | |
| 4,167,283 A | * | 9/1979 | Feldman | 294/1.2 |
| 6,401,915 B1 | * | 6/2002 | Faxe | 206/5.1 |
| 8,231,156 B2 | | 7/2012 | Armwood | |
| 2002/0158477 A1 | * | 10/2002 | Faxe et al. | 294/1.2 |
| 2007/0261970 A1 | * | 11/2007 | Stull | 206/5.1 |
| 2010/0136499 A1 | * | 6/2010 | Gydesen et al. | 433/49 |
| 2012/0140180 A1 | | 6/2012 | Futamura | |

OTHER PUBLICATIONS

Product information on Iensvue2TM Brand Viewer Applicator, softsert+plusTM remover/applicator, and original softsertTM Soft Lens Applicator. 2 pages. http://www.softsert.com. Softsert Inc., Rye Brook, NY.
"Contact Lens Insertion Device." Information sheet. 2 pages. Obtained online at http://www.colouredcontactlenses.org.uk/Contact-Lens-Insertion-Device.html. Coloured Contact Lenses, Durham, UK.
Application instructions, User Guide for softsertTM Soft Lens Applicator. Obtained online at http://www.softsert.com/softsert/softsert-user-guide.html. Softsert Inc., Rye Brook, NY.

(Continued)

*Primary Examiner* — Todd E Manahan
*Assistant Examiner* — Majid Jamialahmadi
(74) *Attorney, Agent, or Firm* — Coats & Bennett, P.L.L.C.

(57) ABSTRACT

An applicator for inserting an enlarged lens onto the eye of a user. The applicator generally includes a receptacle that receives the lens, and a band configured to be worn on the finger of the user. The applicator is shaped and sized for the user to more precisely control the lens during insertion into the eye.

19 Claims, 7 Drawing Sheets

(56) References Cited

OTHER PUBLICATIONS

Softsert+plusTM remover/applicator information sheet page. 1 page. Obtained online at http://store.softsert.com/ssp.html. Softsert Inc., Rye Brook, NY.

DMV Original Contact Lens Remover for Hard & Rigid Gas Permeable Lenses information sheet page. 1 page. http://www.west-op.com/dmvtradharrg.html. Western Opthalmics Corporation, Lynnwood, WA.

O-Ring, PTFE, AS568A-336, Round, PK 2. Product information sheet, 2 pages. http://www.grainger.com/Grainger, Lake Forest, IL.

CLE contact lenses—DMV Soft Contact Lens Handler. Product information sheet, 5 pages. http://clecontactlenses.com/cgi-bin/shop.plx/page=accessories.html. clecontactlenses.com, White Plains, NY.

* cited by examiner

APPLICATOR FOR INSERTING AN ENLARGED LENS ONTO AN EYE OF A USER

REFERENCE TO RELATED APPLICATION

The present application claims priority to U.S. provisional application 61/630,281 filed on Dec. 8, 2011 and entitled "Sclera Contact Lens Applicator Ring", which is herein incorporated by reference in its entirety.

BACKGROUND

Various types of enlarged lenses are worn by persons for both medical and aesthetic reasons. One type is a scleral lens which is large diameter lens sized to rest on the sclera of the eye (i.e., the white portion of the eye). The lens is configured to create a reservoir that extends over and bulges away from the cornea. This reservoir is filled with fluid which fills in irregularities in the cornea thus allowing for improved vision. The fluid-filled reservoir formed against the cornea provides comfort for users who are not able to wear standard contact lenses.

Another type of enlarged lens is a hybrid contact lens that includes a central section surrounded by a skirt. The inclusion of these two different sections in this lens gives it a larger diameter than standard contact lenses. The central section bulges outward and is designed to hold fluid against the user's cornea. The center section may also be gas-permeable and relatively rigid relative to the soft skirt. Hybrid contact lenses are often worn by users that are unable to wear standard rigid gas-permeable contact lenses.

These enlarged lenses are used for a variety of different purposes, including to improve the vision of the wearer, reduce pain in persons with a variety of eye disorders or injuries, and to address light sensitivity for the wearer. Lenses may also be worn for purely aesthetic purposes, such as to create special effects for use in movies or for use with costumes.

Insertion of enlarged lenses is often difficult due to their relatively large size and/or the requirement that the lens be filled with liquid prior to insertion. The user is required to place the lens in an initial orientation with the concave surface facing upward. This orientation provides for the lens to be filled with liquid. Once filled, the user leans over the lens and inserts the lens in an upward motion into their eye. The upward motion is necessary to align the lens with the eye, and to minimize the liquid from spilling from the lens.

A variety of different types of applicators have been used for insertion of enlarged lenses. One type includes a plunger with an opening that is held against an exterior of the lens. The plunger is squeezed by the user to create a suction force to attach the lens. Once the lens is positioned onto the eye, the plunger is squeezed again to release the lens. Other devices have included a variety of supporting surfaces to contact the lens and handles for grasping by the user. However, these prior devices are either difficult to maneuver with the liquid-filled lens, do not adequately release the lens, and/or do not adequately support the lens.

SUMMARY

The present application is directed to an applicator for inserting an enlarged lens onto an eye of a user. The applicator includes a compact shape that is worn on the user's finger and provides for inserting the lens using a natural motion towards the eye. Further, the compact shape provides enhanced control of the applicator during the insertion process.

One embodiment of an applicator includes a receptacle configured to support the enlarged lens during insertion onto the eye. The receptacle includes a concave upper surface configured to contact the enlarged lens and an opposing substantially convex lower surface. The applicator also includes a substantially circular band connected to the receptacle and formed by first and second sections that are separated by a gap positioned opposite from the receptacle. The band includes an inner edge spaced away from the convex lower surface and an outer edge that intersects with the convex lower surface such that the band is positioned at the receptacle.

The band may have a constant thickness along a majority of the length with the thickness being measured between the inner and outer edges. The receptacle may include a circular outer rim having a rounded edge to prevent damage to at least one of the eye and the lens. The receptacle may further include raised splines that extend upward above the concave upper surface. The splines may be evenly distributed about the concave upper surface. Each of the splines may include a straight shape that overlaps at a center of the concave upper surface. The splines may be spaced away from an outer rim of the receptacle.

Another embodiment of the applicator includes a receptacle configured to support the enlarged lens during insertion onto the eye. The receptacle includes a concave floor configured to contact the enlarged lens. A band is connected to the receptacle and includes an opening sized to receive a finger of the user and has a substantially circular inner edge. A distance between a first line tangent to the concave floor and a second line parallel to the first line and tangent to the inner edge is between about 0.5 mm and about 15 mm.

The receptacle may include a maximum depth at a center of the receptacle of between about 2 mm and about 3 mm. The band may include a gap formed between ends of opposing first and second curved sections, with the first and second curved sections each including a common length. The receptacle may include raised splines that extend upward above the concave floor. The splines may be evenly distributed about the concave upper surface. Each of the splines may include a straight shape that overlaps at a center of the concave upper surface. The splines may be spaced away from an outer rim of the receptacle. The receptacle may include a circular shape with a diameter of between about 10 mm and about 20 mm.

Another embodiment of the applicator includes a receptacle configured to support the enlarged lens during insertion onto the eye. The receptacle includes a concave upper surface configured to contact the enlarged lens and an opposing convex lower surface. The upper surface includes a radius of between about 12 mm and about 15 mm. A plurality of splines are positioned within the receptacle and extend above the concave upper surface. A substantially circular band is connected to the receptacle and is formed by first and second curved sections that are separated by a gap positioned opposite from the receptacle. The band includes a substantially circular inner edge spaced away from the convex lower surface. A distance between a first line tangent to the concave upper surface and a second line parallel to the first line and tangent to the inner edge is between about 0.5 mm and about 15 mm.

The receptacle may include a maximum depth of between about 2 mm and about 3 mm. The receptacle may include a diameter of between about 10 mm and about 20 mm. A distance between an upper rim of the receptacle and the inner edge of the band may be between about 2.5 mm and about 18 mm.

The various aspects of the various embodiments may be used alone or in any combination, as is desired.

DETAILED DESCRIPTION

The present application is directed to an applicator for inserting an enlarged lens onto the eye of a user. The applicator generally includes a receptacle that receives the lens, and a connector configured to be worn on the finger of the user. The applicator is shaped and sized for the user to more precisely control the lens during insertion into the eye.

Figure 1:
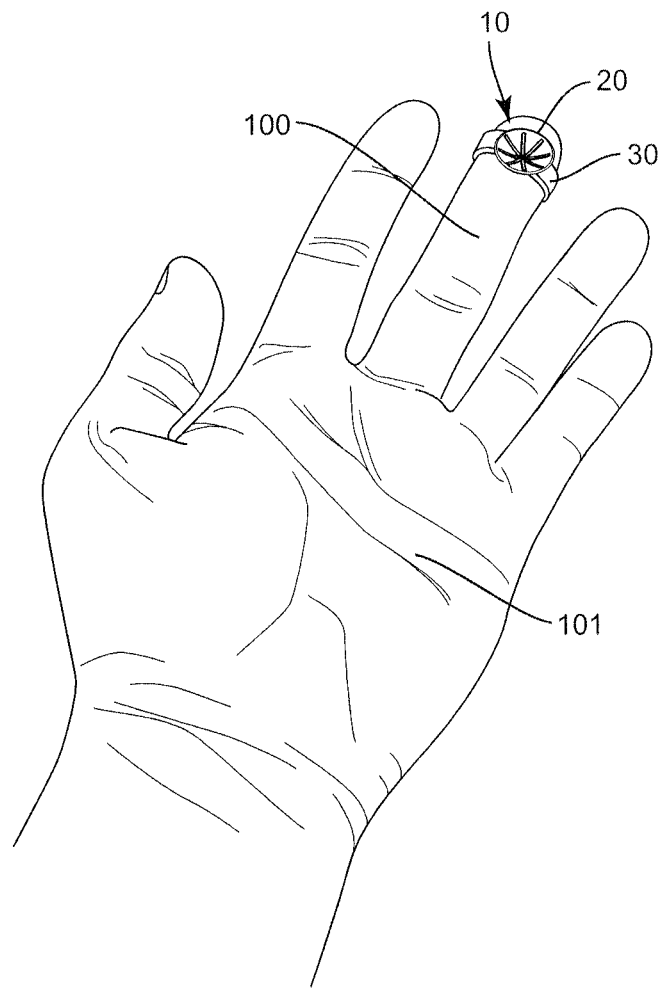
FIG. 1 is a perspective view of an applicator positioned on a user's finger.
Figure 2:
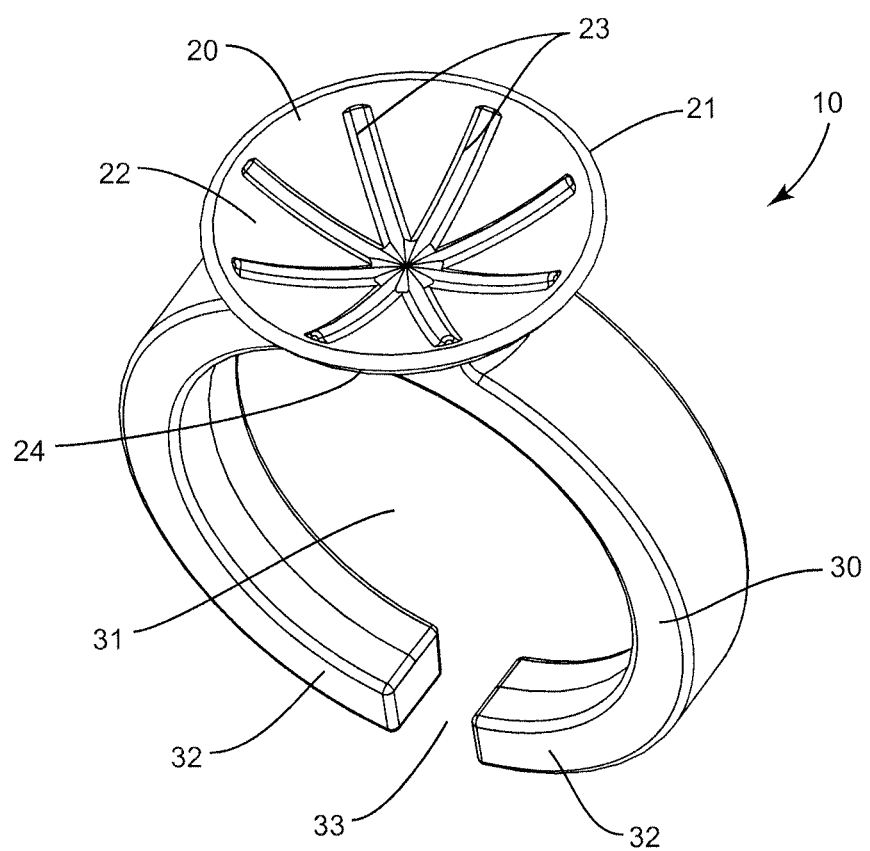
FIG. 2 is a perspective view of an applicator.

FIG. 1 illustrates an applicator 10 being worn by a user. The applicator 10 includes a receptacle 20 that holds the lens and a band 30 sized to be worn on a user's finger 100. The insertion device 10 is worn with the band 30 around the finger 100 and the receptacle 20 facing inward in the direction of the user's palm 101. This orientation provides for a natural movement by the user to maintain the applicator in this upward position to maintain the liquid within the lens and the lens on the receptacle while moving the lens to the eye. Further, the applicator 10 includes a compact shape with the receptacle 20 in close proximity to the band 30 to facilitate insertion of the lens into the user's eye.

The applicator 10 is used for enlarged lenses, such as a scleral lens and hybrid lens. These enlarged lenses extend across the cornea and contact against the sclera of the eye. The average diameter of the cornea is about 11.8 mm. In one embodiment, these lenses have a diameter within a range of about 12 mm to about 25 mm.

Figure 3:
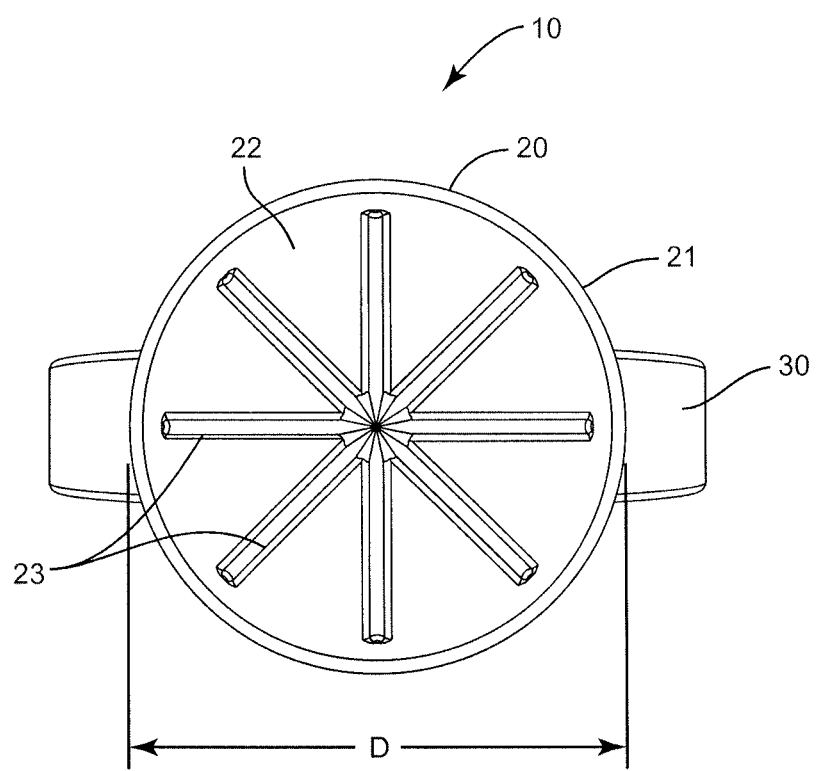
FIG. 3 is a top view of an applicator.
Figure 4:
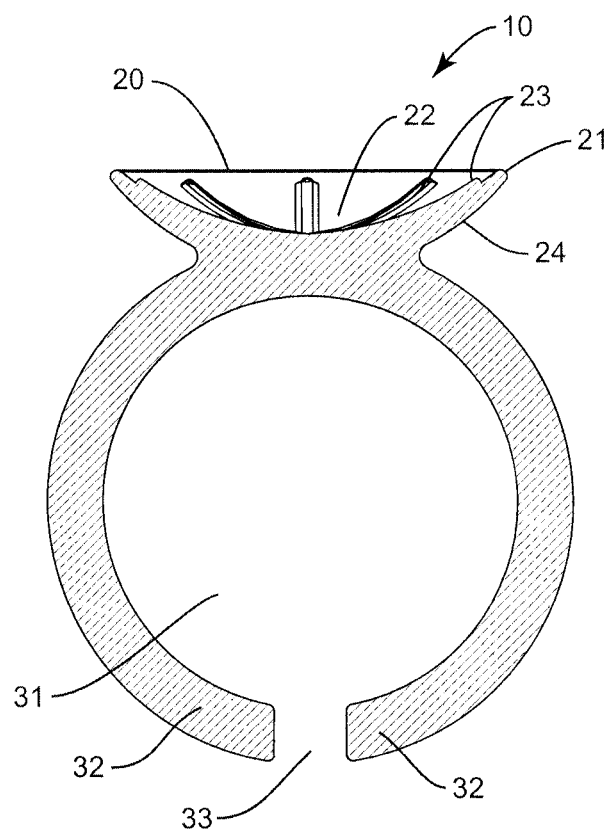
FIG. 4 is a sectional view of an applicator cut along line X-X of FIG. 2.
Figure 5:
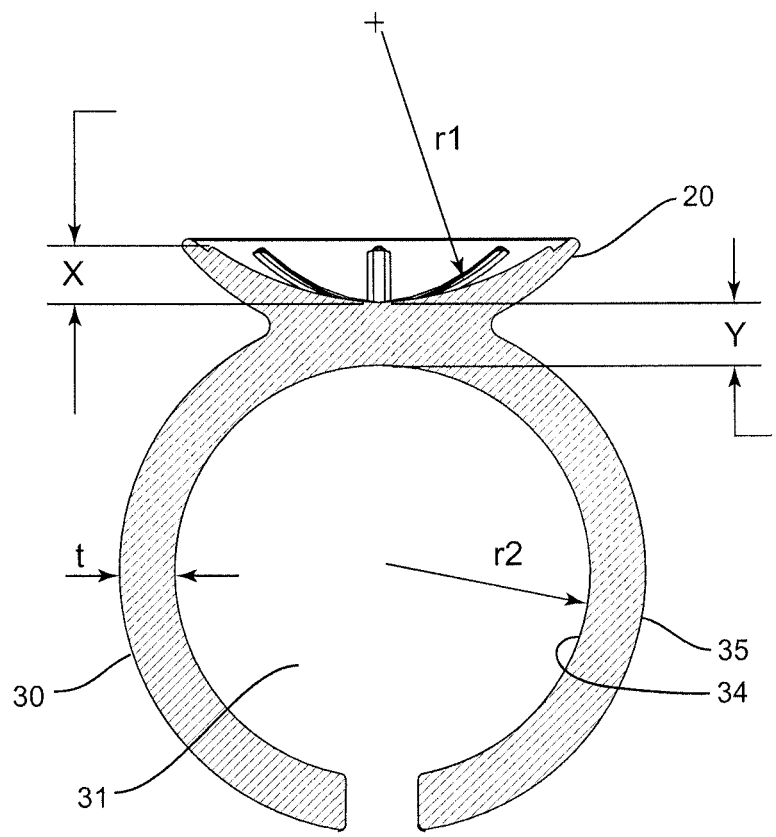
FIG. 5 is a sectional view of an applicator cut along line X-X of FIG. 2 and illustrating a depth of the receptacle and a distance between the receptacle and the opening in the band.

FIGS. 2, 3, 4, and 5 illustrate an applicator 10 for use with an enlarged lens. The applicator 10 generally includes a receptacle 20 to hold the lens. The receptacle 20 includes a circular shape when viewed from the top as illustrated in FIG. 3. The receptacle 20 includes a diameter D that may vary in size depending upon the lens. In some embodiments, the diameter D of the receptacle 20 may range from between about 10 mm and about 20 mm. In one specific embodiment, the diameter D is about 15 mm. The outer rim 21 of the receptacle 20 may be rounded as best illustrated in FIGS. 4 and 5. The rounded shape prevents any sharp edges from potentially contacting the lens or the user's eye during the insertion process.

The receptacle 20 includes a floor 22 with a concave shape that faces away from the band 30. The floor is solid with no openings. The concave floor 22 includes a constant radius r1 across the entirety of the receptacle 20. The radius r1 of the concave floor 22 may range from between about 12 mm and about 15 mm. In one specific embodiment, the radius r1 is about 12 mm.

The depth x of the receptacle 20 is measured between the rim 21 of the receptacle 20 and the concave floor 22. The maximum depth is positioned at the center of the receptacle. FIG. 5 illustrates the maximum depth x between the top rim of the receptacle 20 and a line tangent to the concave floor 22 at the center of the receptacle 20. The depth x may range from between about 2 mm and about 3 mm. In one embodiment, the depth x is about 2 mm.

In one embodiment as illustrated in FIG. 4, a groove 23 may be positioned around the perimeter of the receptacle 20 at the rim 21. The groove 23 provides for a raised surface interfacing with the surface of the lens, such as to prevent the adherence of the lens to the floor 22 of the receptacle 20.

The floor 22 of the receptacle 20 is substantially smooth. Further, one or more splines 23 extend upward above the floor 22. The splines 23 may include a rounded upper edge to prevent any potential damage to the user or the lens during the insertion process. The splines 23 may be arranged in a variety of configurations. In one embodiment as best illustrated in FIG. 3, each of the splines 23 is substantially straight and overlap at a center of the receptacle 20. In this embodiment, the splines 23 form an asterisk shape. The different splines 23 may include the same or different shapes and/or sizes. In one embodiment, the splines 23 may be spaced away from the rim 21 of the receptacle 20.

Figure 6:
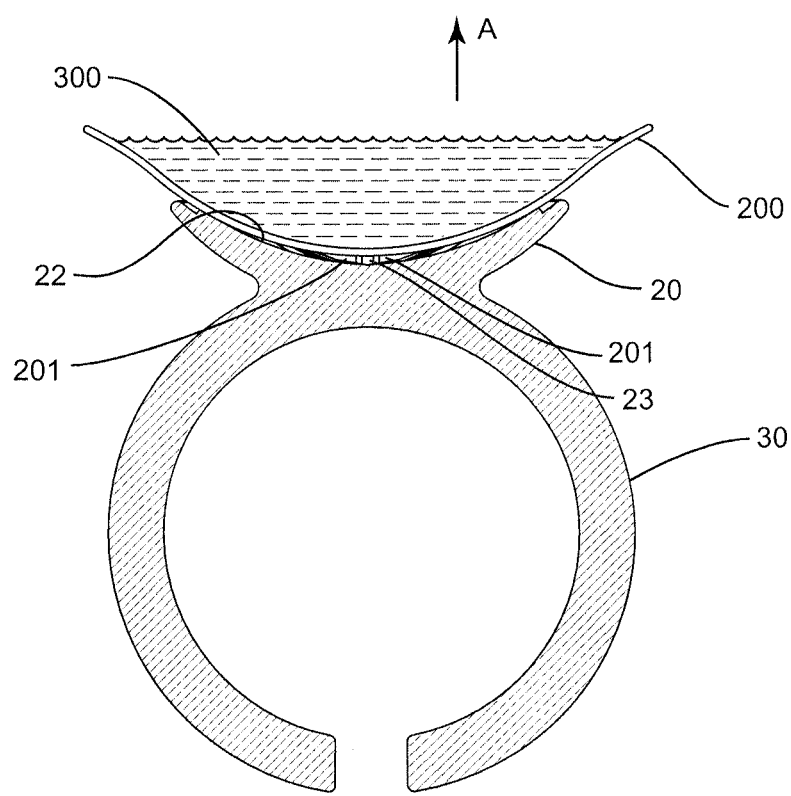
FIG. 6 is a sectional view of a lens positioned in a receptacle of an applicator.

As illustrated in FIG. 6, the lens 200 rests in the receptacle 20 and contacts against the floor 22 and splines 23. Gaps 201 are formed between the lens 200 and the floor 22 adjacent to the splines 23. These gaps 201 reduce or eliminate the lens 200 from becoming stuck to the floor 22. The receptacle 20 is further configured to allow the lens 200 to move relative to the receptacle 20 to align and position the lens 200 within the user's eye.

The exterior 24 of the receptacle 20 includes a substantially convex shape. The exterior 24 may substantially match the floor 22 providing a relatively constant wall thickness inward from the rim 21. The exterior 24 angles away from the floor 22 a greater amount towards the band 30 providing for increased wall thickness along the interior of the receptacle 20.

The band 30 is attached to a lower side of the receptacle 20 and includes an opening 31 for receiving the user's finger 100. The band 30 includes a curved shape formed by a pair of matching curved sections 32 that are separated by a gap 33. The band 30 includes an inner edge 34 and an outer edge 35. The inner edge 34 is spaced away from the exterior 24 of the receptacle 20, and the outer edge 35 intersects with the exterior 24 as illustrated in FIG. 5. As illustrated in FIG. 5, the band 30 may include a substantially constant thickness t measured between the inner and outer edges.

The opening 31 is formed within the inner edge 344 and includes a substantially circular shape with a radius r2. The radius r2 may range between about 7 mm and about 8 mm. In one embodiment, the radius r2 is about 8 mm.

The gap 33 provides for the sections 32 to be flexible to extend around fingers 100 of various sizes. The gap 33 may include various sizes itself.

The applicator 10 has a compact design with the receptacle 20 in close proximity to the band 30. This design provides for increased control by the user because the lens within the receptacle 20 is in close proximity to the user's finger 100. As illustrated in FIG. 5, a distance y measured between a first line tangent to the concave floor 22 and a second line tangent to the inner edge 34 of the opening 31 is between about 0.5 mm and about 15 mm. In one embodiment, the distance y is about 2 mm. In one embodiment, a distance measured between the rim 21 of the receptacle 20 and the inner edge 34 of the opening 31 is between about 2.5 mm and about 18 mm.

Figure 7:
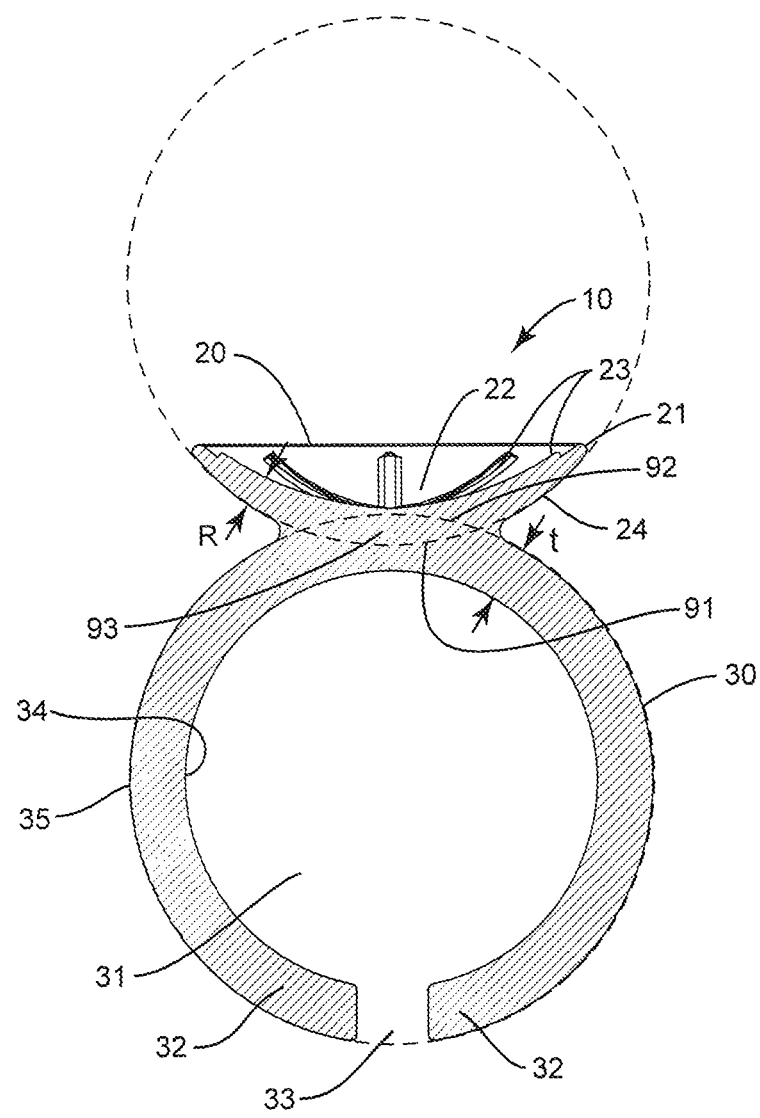
FIG. 7 is a sectional view of an applicator cut along line X-X of FIG. 2 and illustrating an overlap region between the receptacle and the band.

The applicator 10 is designed for the concave floor of the receptacle 20 to be in close physical proximity to the band 30. This close proximity provides control to the user when inserting the lens onto their eye. The applicator 10 includes a design in which the receptacle 20 and band 30 merge together. As illustrated in FIG. 7, the receptacle 20 includes a wall thickness R where it connects with the band 30. The thickness R is measured between the floor of the receptacle 20 and the exterior 24. FIG. 7 illustrates with a dashed line a continuation 91 of the exterior 24 within the merged portion with the band 30. Likewise, the band 30 includes a wall thickness t where it connects with the receptacle 20. The thickness t is measured between the inner edge 34 and the outer edge 35 of the band 30. FIG. 7 also illustrates in dashed lines a continuation 92 of the outer edge 35 through the merged portion. In one embodiment as illustrated in FIG. 7, the exterior 24 and continuation 91 extend along a circle that is formed by the receptacle 20, and the outer edge 35 and continuation 92 extend along a circle formed by the band 30.

As illustrated in FIG. 7, the compact design of the applicator 10 includes an overlap area 93 that is formed between the continuation lines 91, 92. The continuation 91 of the outer edge 24 of the receptacle 20 overlaps beyond the continuation 92 of the outer edge 35 of the band 30 (and the continuation 92 of the outer edge 35 overlaps beyond the continuation 91 of the outer edge 24). In one embodiment, the amount of overlap is at least 25% of the wall thickness R of the receptacle 20.

In use, the applicator 10 is positioned on the user's finger 100 as illustrated in FIG. 1. The receptacle 20 is in an upward position facing away from the user's finger 100. As illustrated in FIG. 6, the user places the lens 200 into the receptacle 20 with the outer surface of the lens contacting against the splines 23 and the floor 22. The solid floor 22 prevents the lens 200 from partially or completely falling through the receptacle 20.

Depending upon the size of the receptacle 20 and the lens 200, the lens 200 may extend outward beyond the rim 21. This difference in size is illustrated in the embodiment of FIG. 6 with the diameter of the receptacle 20 being smaller than that of the lens 200. This relative sizing results in the outer rim of the lens 200 extending radially outward beyond the rim 21 of the receptacle 20. Other embodiments may include the lens 200 being smaller than and positioned within the interior of the receptacle rim 21.

With the lens 200 in the receptacle 20, the user fills the lens 200 with fluid 300. The orientation of the receptacle 20 and lens 200 provides for the fluid 300 to be retained within the lens 200. The amount of fluid 300 may depend upon a variety of factors, including the type of lens 200 and the preference of the user.

The user next leans over and positions their head above the applicator 10. The user then moves the applicator 10 upward in the direction of arrow A towards the user's eye. This upward movement maintains the fluid within the lens 200 and the lens 200 on the receptacle 20. The user continues to move the applicator 10 upward and aligns the lens 200 with their eye. The user than manipulates the applicator 10 to place the lens 200 onto their eye. The applicator 10 maintains the orientation of the lens 200 and provides rotational positioning of the lens upon contact with the eye. Once the lens 200 is removed from the applicator 10, the user can move the applicator 10 away.

The design of the applicator 10 makes it easier for the user to insert the lens 200. The design simplifies the insertion of the lens 200 by capitalizing on the "natural" motion (and orientation) of the finger relative to the eye. The design of the applicator 10 and resulting technique mirror the natural movement of the finger to the eye in rotational control and proper orientation of the lens 200 thus making it easier for the user.

Further, the concave shape of the receptacle 20 allows for the natural rotation of the lens 200 relative to the receptacle 20 once the lens 200 is in contact with the eye. This allows for the lens 200 to properly contour to and be positioned relative to the eye. The relative movement of the lens 200 within the receptacle 20 minimizes or eliminates the adverse effects of the ever-changing positioning of the finger and applicator 10 on approach to the surface of the eye.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc. and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. An applicator for inserting an enlarged lens onto an eye of a user, the applicator comprising:
   a receptacle configured to support the enlarged lens during insertion onto the eye, the receptacle including a concave upper surface configured to contact the enlarged lens and an opposing substantially convex lower surface; and
   a substantially circular band connected to the receptacle and formed by first and second sections that are separated by a gap positioned opposite from the receptacle, the band including an inner edge spaced away from the convex lower surface and an outer edge that intersects with the convex lower surface such that the band is positioned at the receptacle;
   the receptacle and the band being connected together at a connection portion, the connection portion comprising an overlap section in which a continuation of the lower surface of the receptacle overlaps with a continuation of the outer edge of the band;
   the connection portion extending between a first line tangent to a floor of the receptacle and a second line parallel to the first line and tangent to the inner edge of the ring;
   a ratio of a length of the connection portion between the first and second lines to a diameter of the receptacle ranging between about 0.025 to about 1.5.

2. The applicator of claim 1, wherein the band includes a constant thickness along a majority of the length, the thickness being measured between the inner and outer edges.

3. The applicator of claim 1, wherein the receptacle includes a circular outer rim having a rounded edge to prevent damage to at least one of the eye and the lens.

4. The applicator of claim 1, wherein the receptacle further includes raised splines that extend upward above the concave upper surface.

5. The applicator of claim 4, wherein the splines are evenly distributed about the concave upper surface.

6. The applicator of claim 4, wherein each of the splines includes a straight shape that overlaps at a center of the concave upper surface.

7. The applicator of claim 4, wherein the splines are spaced away from an outer rim of the receptacle.

8. An applicator for inserting an enlarged lens onto an eye of a user, the applicator comprising:
   a receptacle configured to support the enlarged lens during insertion onto the eye, the receptacle including a concave floor configured to contact the enlarged lens; and
   a band connected to the receptacle and including an opening sized to receive a finger of the user and having a substantially circular inner edge;
   a distance between a first line tangent to the concave floor and a second line parallel to the first line and tangent to the inner edge being between about 0.5 mm and about 15 mm.

9. The applicator of claim 8, wherein the receptacle includes a maximum depth at a center of the receptacle of between about 2 mm and about 3 mm.

10. The applicator of claim 8, wherein the band includes a gap formed between ends of opposing first and second curved sections, the first and second curved sections each including a common length.

11. The applicator of claim 8, wherein the receptacle further includes raised splines that extend upward above the concave floor.

12. The applicator of claim 11, wherein the splines are evenly distributed about the concave upper surface.

13. The applicator of claim 11, wherein each of the splines includes a straight shape that overlaps at a center of the concave upper surface.

14. The applicator of claim 11, wherein the splines are spaced away from an outer rim of the receptacle.

15. The applicator of claim 8, wherein the receptacle includes a circular shape with a diameter of between about 10 mm and about 20 mm.

16. An applicator for inserting an enlarged lens onto an eye of a user, the applicator comprising:
   a receptacle configured to support the enlarged lens during insertion onto the eye, the receptacle including a concave upper surface configured to contact the enlarged lens and an opposing convex lower surface, the upper surface including a radius of between about 12 mm and about 15 mm and a diameter of between about 10 mm and about 20 mm; and
   a plurality of splines positioned within the receptacle and extending above the concave upper surface;
   a substantially circular band connected to the receptacle and formed by first and second curved sections that are separated by a gap positioned opposite from the receptacle, the band including a substantially circular inner edge spaced away from the convex lower surface;
   a distance between a first line tangent to the concave upper surface and a second line parallel to the first line and tangent to the inner edge being between about 0.5 mm and about 15 mm;
   a connection portion extending between a first line tangent to a floor of the receptacle and a second line parallel to the first line and tangent to the inner edge of the ring;
   a ratio of a length of the connection portion between the first and second lines to a diameter of the receptacle ranging between about 0.025 to 1.5.

17. The applicator of claim 16, wherein the receptacle includes a maximum depth of between about 2 mm and about 3 mm.

18. The applicator of claim 16, wherein the receptacle includes a diameter of between about 10 mm and about 20 mm.

19. The applicator of claim 16, wherein a distance between an upper rim of the receptacle and the inner edge of the band being between about 2.5 mm and about 18 mm.

\* \* \* \* \*